(12) United States Patent
Bodnar et al.

(10) Patent No.: US 11,318,085 B2
(45) Date of Patent: May 3, 2022

(54) METHODS, SYSTEMS AND KITS FOR IMPROVING SKIN APPEARANCE AND BOOSTING PHOTOPROTECTION

(71) Applicant: L'OREAL, Paris (FR)

(72) Inventors: Brian Scott Bodnar, Manasquan, NJ (US); Anne-Laure Suzanne Bernard, New York, NJ (US); Anil Shah, East Windsor, NJ (US); Alexandra Jane Elisa Farran, Dayton, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/146,117

(22) Filed: Sep. 28, 2018

(65) Prior Publication Data

US 2020/0101007 A1    Apr. 2, 2020

(51) Int. Cl.
| | |
|---|---|
| *A61K 8/90* | (2006.01) |
| *A61K 8/81* | (2006.01) |
| *A61K 8/29* | (2006.01) |
| *A61K 8/25* | (2006.01) |
| *A61K 8/35* | (2006.01) |
| *A61K 8/37* | (2006.01) |
| *A61Q 17/04* | (2006.01) |
| *A61Q 19/00* | (2006.01) |

(52) U.S. Cl.
CPC ............... *A61K 8/90* (2013.01); *A61K 8/25* (2013.01); *A61K 8/29* (2013.01); *A61K 8/35* (2013.01); *A61K 8/37* (2013.01); *A61K 8/8152* (2013.01); *A61Q 17/04* (2013.01); *A61Q 19/00* (2013.01); *A61K 2800/413* (2013.01); *A61K 2800/43* (2013.01); *A61K 2800/592* (2013.01); *A61K 2800/594* (2013.01); *A61K 2800/884* (2013.01)

(58) Field of Classification Search
CPC ............................... A61Q 17/04; A61Q 19/00
See application file for complete search history.

(56) References Cited

U.S. PATENT DOCUMENTS

| | | |
|---|---|---|
| 2017/0189317 A1 | 7/2017 | Bernard |
| 2017/0189321 A1 | 7/2017 | Bernard |
| 2018/0015023 A1 | 1/2018 | Bernard |

FOREIGN PATENT DOCUMENTS

JP     2006036704 A  *  2/2006

* cited by examiner

*Primary Examiner* — Gina C Justice
(74) *Attorney, Agent, or Firm* — Laetitia Leproust; Robert Klemz

(57) ABSTRACT

The present disclosure relates to methods, systems and kits for treating the skin by applying onto the skin a skin tightening composition comprising 1) at least one thermoplastic elastomer and at least one adhesive polymer; and 2) a sunscreen composition comprising one or more UV filters. Methods, systems and kits comprise applying the compositions of the systems sequentially.

14 Claims, No Drawings

METHODS, SYSTEMS AND KITS FOR IMPROVING SKIN APPEARANCE AND BOOSTING PHOTOPROTECTION

FIELD OF THE DISCLOSURE

The present disclosure relates to methods, systems and kits for boosting the SPF in skin tightening compositions.

BACKGROUND

Skin is primarily comprised of two layers. The outer layer, or epidermis, has a depth of approximately 100 µm. The inner layer, or dermis, has a depth of approximately 3000 µm from the outer surface of the skin and is comprised of a network of fibrous protein known as collagen, which provides skin firmness, and elastin, which supplies skin elasticity and rebound. As a person ages, their skin produces less collagen and elastin each year, which can cause under eye wrinkles, eye bags, crow's feet, and forehead wrinkles to appear.

Additionally, exposure to the sun can cause a person's skin to age prematurely—a process referred to as "photoaging." Exposure to the sun's ultraviolet (UV) rays can damage the skin, causing dryness, deep wrinkles, accentuated skin furrows, loss of elasticity, and mottled pigmentation even earlier than would be seen by aging alone.

As a result of the aging process and UV exposure, the skin becomes thinner and more fragile over time, and wrinkle formation as a result is inevitable.

In addition to wrinkles, as a person ages, other skin imperfections may appear or become more noticeable. For example, age spots, which are brown or gray sun-induced skin lesions, may appear on sun-exposed skin as a person gets older. It is common for consumers to wish to improve the appearance of such age related skin imperfections such as wrinkles, crow's feet, age-spots, eye bags, and the like. Additionally, many consumers wish to improve the appearance of, or hide, other skin imperfections such as acne, scars, enlarged pores, and so on, which may not be related to aging or sun exposure.

As such, there is a consumer desire for cosmetic formulations that are effective at reducing the appearance of the aforementioned skin imperfections, while providing effective UV protection to prevent further damage to the skin from the sun.

SUMMARY OF THE DISCLOSURE

The methods, systems and kits of the instant case provide a surprising improvement in sun protection factor ("SPF") while simultaneously improving the appearance of skin. The methods, systems and kits include applying onto the skin a skin tightening composition and a sunscreen composition. The surprising improvement in SPF occurs regardless of the order of application, i.e., the skin tightening composition can be applied first followed by application of the sunscreen compositions or vice versa.

In addition to boosting the SPF, which provides full spectrum photo-protection to the skin, the methods provide an immediate and dramatic improvement to the appearance of skin, for example, by reducing the appearance of wrinkles, eye bags, pores, and skin imperfections such as scarring, dark spots (and uneven skin tone), dark circles, and roughness. This results from application of the skin tightening compositions, which includes at least one thermoplastic elastomer, at least one adhesive and at least one filler.

Unlike other products, the films formed on the skin do not dry-out, whiten, crack, or peel. Instead, they remain flexible (elastic), durable, and comfortable. Moreover, the compositions (and resulting films) hydrate and protect the underlying skin. When the skin tightening composition and sunscreen composition are combined together before application to skin, the result only yields a boost to the SPF, whereas examples of the instant case uniquely allow for boosting the SPF and simultaneously improve the appearance of the skin when both compositions are layered onto the skin, regardless of the order of application. The skin tightening compositions typically include:

i. at least one thermoplastic elastomer chosen from amorphous hydrocarbon block copolymers of styrene and monomers of hydrocarbon containing 2 to 5 carbon atoms and comprising one or two ethylenic unsaturations, and having a first Tg below about 0° C., and a second Tg greater than about 25° C.;
ii. at least one adhesive film-forming polymer chosen from polymer particles of C1-C4 alkyl(methacrylate)polymer, stabilized in a non-aqueous dispersion; and
iii. at least one filler,
wherein the Young Modulus of the film formed on the skin is greater than about 500 kPa.

In some embodiments, the methods of the instant disclosure for treating the skin by applying onto the skin typically include the following:

(a) a skin tightening composition comprising:
at least one thermoplastic elastomer chosen from amorphous hydrocarbon block copolymers of styrene and monomers of hydrocarbon containing 2 to 5 carbon atoms and comprising one or two ethylenic unsaturations, and having a first Tg below about 0° C., and a second Tg greater than about 25° C.;
at least one adhesive film-forming polymer chosen from polymer particles of C1-C4 alkyl(methacrylate)polymer, stabilized in a non-aqueous dispersion; and at least one filler,
(b) a sunscreen composition comprising:
one or more UV filters; and
a cosmetically acceptable carrier,
wherein the Young Modulus of the film formed on the skin is greater than about 500 kPa,
wherein the skin tightening and the sunscreen are layered.

In one embodiment, the instant disclosure relates to methods wherein the skin tightening composition is applied onto the skin, followed by application of the sunscreen composition onto the skin tightening composition.

In some embodiments, the instant disclosure relates to methods wherein the sunscreen composition is applied onto the skin, followed by application of the skin tightening composition onto the sunscreen composition.

In some embodiments, the instant disclosure relates to methods wherein applying the skin tightening composition over the sunscreen composition increases the SPF in vitro by about 25 times relative to the application of the sunscreen composition alone.

In some embodiments, the instant disclosure relates to methods wherein applying the sunscreen composition over the skin tightening composition increases the SPF in vitro by about 25 25 times relative to the application of the sunscreen composition alone.

In some embodiments, the instant disclosure relates to methods wherein applying the skin tightening composition over the sunscreen composition increases the SPF in vitro more than the SPF in vitro obtained by applying a mixture of the skin tightening composition and the sunscreen composition in the same ratio as the layered application of the skin tightening composition and the sunscreen composition.

In various embodiments, the instant disclosure relates to methods wherein applying the sunscreen composition over the skin tightening composition increases the SPF in vitro more than the SPF in vitro obtained by applying a mixture of the skin tightening composition and the sunscreen composition in the same ratio as the layered application of the skin tightening composition and the sunscreen composition.

In one embodiment, the instant disclosure relates to methods wherein the at least one thermoplastic elastomer is present in the composition in an amount ranging from about 5% to about 25% by weight, relative to the total weight of the composition.

In further embodiments, the instant disclosure relates to methods wherein the one or more UV filters are organic chemical filters. In some embodiments, the instant disclosure relates to methods wherein the one or more UV filters are selected from the group consisting of of ethylhexyl salicylate, butyl methoxydibenzoylmethane, ethylhexyl methoxycinnamate, octocrylene, phenylbenzimidazole sulfonic acid, terephthalylidene dicamphor sulfonic acid, benzophenone-3, benzophenone-4, benzophenone-5,4-methylbenzylidene camphor, benzimidazilate, anisotriazine, ethylhexyl triazone, diethylhexyl butamido triazone, methylene bis-benzotriazolyl tetramethylbutylphenol, drometrizole trisiloxane, and mixtures thereof.

In one embodiment, the instant disclosure relates to methods wherein the sunscreen composition comprises at least two organic UV filters. In various embodiments, the instant disclosure relates to methods wherein the sunscreen composition comprises at least one UVA filter and at least one UVB filter.

In one embodiment, the instant disclosure relates to methods wherein the one or more UV filters are mineral filters. In further embodiments, the instant disclosure relates to methods wherein the one or more UV filters are selected from the group consisting of pigments and nanopigments formed of coated or uncoated metal oxides. In one embodiment, the instant disclosure relates to methods wherein the pigments or nanopigments are selected from the group consisting of coated and uncoated titanium oxide, zinc oxide, iron oxide, zirconium oxide, cerium oxide and mixtures thereof. In one embodiment, the instant disclosure relates to methods wherein the nanopigment is titanium oxide.

In one embodiment, the instant disclosure relates to methods wherein the sunscreen composition is applied topically under the skin tightening composition.

In some embodiments, the instant disclosure relates to methods wherein the sunscreen composition is applied topically over the skin tightening composition.

In some embodiments, the instant disclosure relates to methods wherein the cosmetically acceptable carrier in the sunscreen composition comprises water.

Another aspect of the instant disclosure can include a kit for treating the skin, the kit comprising two separate compositions that are layered on the skin one after the other, the first composition comprising a skin tightening composition and the second composition comprising a sunscreen composition:
a) the skin tightening composition comprising:
i. at least one thermoplastic elastomer chosen from amorphous hydrocarbon block copolymers of styrene and monomers of hydrocarbon containing 2 to 5 carbon atoms and comprising one or two ethylenic unsaturations, and having a first Tg below about 0° C., and a second Tg greater than about 25° C.;
ii. at least one adhesive film-forming polymer chosen from polymer particles of C1-C4 alkyl(methacrylate)polymer, stabilized in a non-aqueous dispersion; and
iii. at least one filler,
b) the sunscreen composition comprising:
iv. one or more UV filters; and
v. a cosmetically acceptable carrier,
wherein the Young Modulus of the film formed on the skin is greater than about 500 kPa;
wherein the skin tightening and the sunscreen are layered.

In some embodiments, the instant disclosure relates to kits comprising application of the skin tightening composition onto the skin, followed by application of the sunscreen composition onto the skin tightening composition.

In some embodiments, the instant disclosure relates to kits comprising application of the sunscreen composition onto the skin, followed by application of the skin tightening composition onto the sunscreen composition.

Another aspect of the instant disclosure can include a system for treating the skin by applying onto the skin:
(a) a skin tightening composition comprising:
i. at least one thermoplastic elastomer chosen from amorphous hydrocarbon block copolymers of styrene and monomers of hydrocarbon containing 2 to 5 carbon atoms and comprising one or two ethylenic unsaturations, and having a first Tg below about 0° C., and a second Tg greater than about 25° C.;
ii. at least one adhesive film-forming polymer chosen from polymer particles of C1-C4 alkyl(methacrylate)polymer, stabilized in a non-aqueous dispersion; and
iii. at least one filler,
(b) a sunscreen composition comprising:
iv. one or more UV filters.
v. A cosmetically acceptable carrier.
wherein the Young Modulus of the film formed on the skin is greater than about 500 kPa;
wherein the skin tightening and the sunscreen are layered.

DETAILED DESCRIPTION OF THE DISCLOSURE

In various embodiments, the instant disclosure relates to methods for treating the skin by applying onto the skin:
(a) a skin tightening composition comprising:
i. at least one thermoplastic elastomer chosen from amorphous hydrocarbon block copolymers of styrene and monomers of hydrocarbon containing 2 to 5 carbon atoms and comprising one or two ethylenic unsaturations, and having a first $T_g$ below about 0° C., and a second $T_g$ greater than about 25° C.;
ii. at least one adhesive film-forming polymer chosen from polymer particles of $C_1$-$C_4$ alkyl(methacrylate) polymer, stabilized in a non-aqueous dispersion; and
iii. at least one filler,
(b) a sunscreen composition comprising:
iv. one or more UV filters; and
v. a cosmetically acceptable carrier,
wherein the Young Modulus of the film formed on the skin is greater than about 500 kPa,
wherein the skin tightening and the sunscreen are layered.

In various embodiments, the disclosure relates to methods for boosting the sun protection factor ("SPF") while simultaneously improving the appearance of skin.

As used herein, the term "boosting" means that the in vitro SPF values are increased compared to the sunscreen composition used alone, and consequently improve the protection of the skin from the sun damages.

As used herein, the term "layered" or "layering" means that the compositions are consecutively applied to the same area of skin, one on top of the other. The order of application is not critical; the skin tightening composition can be applied first or vice versa. The inventors discovered that layering the skin tightening composition and the sunscreen composition onto the skin unexpectedly improved the SPF. In other words, the layered application of the skin tightening composition and the sunscreen composition increases the in vitro SPF more than the in vitro SPF obtained by applying the sunscreen composition alone.

The skin tightening composition may be applied first or the sunscreen composition may be applied first. Similar amounts of the skin tightening composition and sunscreen composition can be applied. For instance, the ratio of skin tightening composition to sunscreen composition applied to the skin may be about 10:1 to about 1:1, about 5:1 to about 2:1, or about 4:1 to about 3:1. The skin tightening compositions and the sunscreen compositions can be layered immediately one on top of the other, as long as care is taken to avoid mixing the two layers. In some instances, it may be desirable to wait for a period of time before layering the skin perfecting composition or the sunscreen composition on top of the other. For example, it can be useful to allow the initial application of the skin tightening composition or the sunscreen composition to dry for a period of time before subsequently layering the skin tightening composition or the sunscreen composition or vice versa. The period of time may be about 1 second to about 20 minutes, about 10 seconds to about 20 minutes, about 30 seconds to about 20 minutes, or about 1 minute to about 20 minutes.

The skin tightening composition and sunscreen composition can be layered onto all areas of the body for which protection and perfection is desired. Nonetheless, the methods are particularly useful for treating the skin of the face, which is often exposed to the sunlight.

In some embodiments, methods of using the skin tightening compositions and the sunscreen compositions by application of the skin tightening composition onto the skin, followed by application of the sunscreen composition onto the skin tightening composition can increase the SPF in vitro by about 25 times compared to application of the sunscreen composition alone. In further embodiments, methods of using the sunscreen compositions and the skin tightening compositions by application of the sunscreen composition onto the skin, followed by application of the skin tightening composition onto the sunscreen composition can increase the SPF in vitro by about 25 times compared to the application of the sunscreen composition alone.

Compositions

According to various embodiments, the compositions comprise at least one thermoplastic elastomer, at least one adhesive polymer, and at least one filler, which together form an association. Additional optional components, such as solvents, silicone elastomers, humectants, and water, may also be included in the compositions.

Thermoplastic Elastomer

According to various exemplary and non-limiting embodiments, the at least one thermoplastic elastomer may be chosen from block copolymers having at least two glass transition temperatures ("$T_g$"). The block copolymers may be hydrocarbon-soluble or dispersible in the oily phase. In various embodiments, the at least one thermoplastic elastomer may be amorphous, crystalline, or semicrystalline.

The block copolymers comprise one or more hard segments attached to one or more soft segments. The hard segments of the thermoplastic elastomer may comprise vinyl monomers in varying amounts. Examples of suitable vinyl monomers include, but are not limited to, styrene, methacrylate, acrylate, vinyl ester, vinyl ether, vinyl acetate, and the like. The soft segments may comprise olefin polymers and/or copolymers which may be saturated, unsaturated, or combinations thereof. Exemplary olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

By way of example, the at least one thermoplastic elastomer may be chosen from diblock, triblock, multiblock, radial, and star copolymers obtained by polymerizing at least one unsaturated hydrocarbon monomer having 2 to 5 carbon atoms and having one or two ethylenic unsaturations. Non-limiting examples of unsaturated hydrocarbon monomers having 2 to 5 unsaturated carbon atoms include ethylene, propylene, butadiene, isoprene or pentadiene. In various exemplary and non-limiting embodiments, block copolymers may be chosen from those comprising at least one styrene block and at least one block comprising units selected from butadiene, ethylene, propylene, butylene, isoprene, or mixtures thereof.

Optionally, the block copolymer may be hydrogenated to reduce the residual ethylenic unsaturation after the polymerization of the monomers. For example, the hydrocarbon-based block copolymer may optionally be a hydrogenated copolymer comprising styrene blocks and ethylene blocks/$C_3$-$C_4$ alkylene or isoprene blocks. In one exemplary embodiment, the block copolymer is an amorphous hydrocarbon block copolymer, for example an amorphous hydrocarbon block copolymer of styrene and monomers of hydrocarbon containing 2 to 5 carbon atoms and comprising one or two ethylenic unsaturations.

The amorphous thermoplastic elastomers comprise at least one first block whose $T_g$ is below about 20° C., such as below about 0° C., below about −20° C., or below about −40° C. The $T_g$ of the first block can, for example, range from about −150° C. to about 20° C., such as from about −100° C. to about 0° C. The block copolymers also comprise at least one second block whose $T_g$ is greater than about 25° C., such as greater than about 50° C., greater than about 75° C., greater than about 100° C., or greater than about 150° C. The $T_g$ of the second block can, for example, range from about 25° C. to about 150° C., such as from about 50° C. to about 125° C., about 60° C. to about 120° C., or about 70° C. to about 100° C.

Exemplary, non-limiting amorphous diblock copolymers may be chosen from styrene-ethylene/propylene copolymers, styrene-ethylene/butadiene copolymers, styrene-ethylene/butylene copolymers, styrene-butadiene, or styrene-isoprene copolymers. Diblock copolymers are sold, for example, under the name Kraton® G1701E by Kraton Polymers.

Exemplary triblock amorphous copolymers may be chosen from styrene-ethylene/propylene-styrene copolymers, styrene-ethylene/butadiene-styrene copolymers, copolymers of styrene-isoprene-styrene, and copolymers of styrene-butadiene-styrene, such as those sold under the names Kraton® G1650, Kraton® D1101, D1102 Kraton®, Kraton® D1160 by Kraton Polymers. In one exemplary embodiment, the thermoplastic elastomer may be a mixture of a triblock copolymer styrene-butylene/ethylene-styrene diblock copolymer and a styrene-ethylene/butylene, such as those sold under the name Kraton® G1657M by Kraton Polymers. In a further example, the thermoplastic elastomer may be a mixture of hydrogenated triblock copolymer styrene-butylene/ethylene-styrene hydrogenated star polymer and ethylene-propylene-styrene, such mixing can in particular be in isododecane in another oil. Such mixtures are sold, for example, by Penreco under the trade names VERSAGEL® M5960 and M5670 VERSAGEL®.

In further exemplary embodiments, the at least one thermoplastic elastomer is chosen from semicrystalline block copolymers having at least two glass transition temperatures. The semicrystalline block copolymers can comprise at least one first block whose $T_g$ is greater than about 40° C., such as greater than about 75° C., or greater than 100° C. The $T_g$ of the first block can, for example, range from about 40° C. to about 150° C., such as from about 50° C. to about 100° C. The semicrystalline block copolymers also comprise at least one second block whose $T_g$ is less than about −50° C., such as less than about −75° C., less than about −100° C., or less than about −150° C. The $T_g$ of the second block can, for example, range from about −150° C. to about −50° C., such as from about −100° C. to about −50° C.

By way of non-limiting example, the semicrystalline thermoplastic elastomers may be chosen from copolymers containing a polyamide and/or a polysilicone and/or a polyurethane, for example polysilicone-polyamides or polysilicone-polyurethanes. For example, the semicrystalline thermoplastic elastomers may be chosen from polyorganosiloxane-containing polymers comprising at least one moiety corresponding to formula I

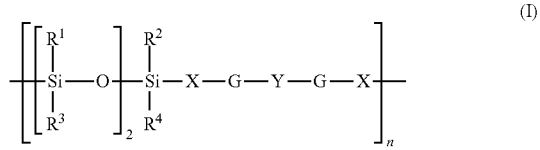

in which:
1) $R^1$, $R^2$, $R^3$ and $R^4$, which may be identical or different, represent a group chosen from: (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, (b) $C_6$ to $C_{10}$ aryl groups, optionally substituted with one or more $C_1$ to $C_4$ alkyl groups, (c) polyorganosiloxane chains possibly containing one or more oxygen, sulphur and/or nitrogen atoms;
2) X, which may be identical or different, represents a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;

4) G, which may be identical or different, represents a group chosen from ester, amide, sulphonamide, carbamate, thiocarbamate, urea, thiourea groups, and combinations thereof;
5) m is an integer ranging from 1 to 1,000, preferably from 1 to 700 and more preferably from 6 to 200; and
6) n is an integer ranging from 2 to 500 and preferably from 2 to 200.

In further embodiments, the semicrystalline thermoplastic elastomers may be chosen from copolymers containing at least one moiety corresponding to formula II:

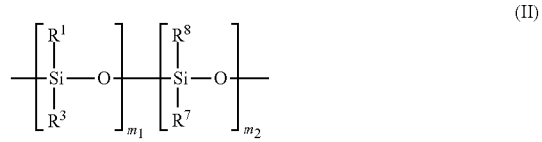

in which:
$R^1$ and R, which may be identical or different, are as defined above for formula (I),
$R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups,
$R^8$ represents a group of formula —X-G-$R^9$ in which X, G and $R^9$ are as defined above,
$m_1$ is an integer ranging from 1 to 998, and
$m_2$ is an integer ranging from 2 to 500.

In yet further embodiments, it is also possible to use a block copolymer comprising several different moieties of formula (I), and/or several different moieties of formula (II), for example a polymer in which at least one of the groups $R^1$, $R^2$, $R^3$, $R^4$, X, G, Y, m, and n is different in one of the moieties. It is also possible to use a block copolymer comprising at least one moiety of formula (I) and at least one moiety of formula (II), the moieties of formula (I) and the moieties of formula (II) possibly being identical to, or different from, each other.

For example, in at least one embodiment, the semicrystalline thermoplastic elastomer may be chosen from polyamide copolymers containing at least one moiety corresponding to formula III and at least one moiety corresponding to formula IV:

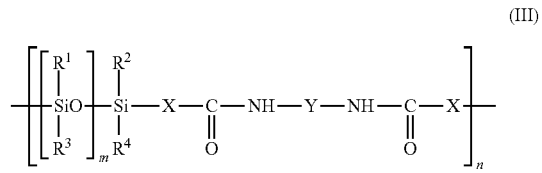

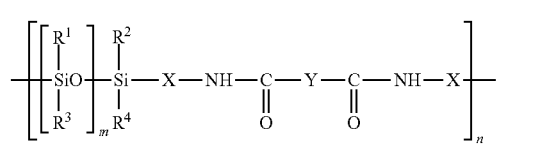

in which:

(a) $R^1$, $R^2$, $R^3$, and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700; and (e) n is a number between 1 and 500.

By way of example only, the semicrystalline thermoplastic elastomer may be chosen from Nylon 6, Nylon 66, and Nylon-611/dimethicone copolymer.

The thermoplastic elastomer may be present in the composition in an amount up to about 25%, such as an amount ranging from about 5% to about 20%, about 6% to about 18%, about 7% to about 16%, about 8% to about 15%, about 9% to about 14%, relative to the weight of the composition.

Adhesive Polymer

Compositions according to the disclosure further comprise at least one adhesive film-forming polymer. In various embodiments, the at least one adhesive polymer may be amorphous, crystalline, or semicrystalline.

In various embodiments, the adhesive polymer may have a $T_g$ greater than about 25° C., such as greater than about 50° C., greater than about 75° C., or greater than about 100° C., according to various embodiments. In further embodiments, the adhesive polymer may have a $T_g$ less than about 25° C., such as less than about 0° C., less than about −25° C., or less than about −50° C.

The at least one adhesive polymer may be present in the composition in an amount up to about 25%, such as an amount ranging from about 5% to about 20%, about 6% to about 18%, about 7% to about 16%, about 8% to about 15%, about 9% to about 14%, or relative to the weight of the composition.

As non-limiting examples of adhesive polymers having a $T_g$ greater than about 25° C. may be mentioned polymer particles of $C_1$-$C_4$ alkyl(methacrylate)polymer, stabilized in a non-aqueous dispersion, referred to herein for ease of reference as an "oil dispersion," such as those described in WO2015/091513 which is incorporated by reference herein.

By way of example, the $C_1$-$C_4$ alkyl (meth)acrylate monomers may be chosen from methyl (meth)acrylate, ethyl (meth)acrylate, n-propyl (meth)acrylate, isopropyl (meth) acrylate, n-butyl (meth)acrylate and tert-butyl (meth)acrylate. For example, the polymer may be a methyl acrylate and/or ethyl acrylate polymer.

The polymer may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof. For example, the ethylenically unsaturated acid monomer may be chosen from (meth) acrylic acid, maleic acid, and maleic anhydride.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula $NH^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles of the oil dispersion may thus comprise or consist essentially of about 80% to about 100%, by weight, of $C_1$-$C_4$ alkyl (meth)acrylate and of about 0% to about 20%, by weight, of ethylenically unsaturated acid monomer, relative to the total weight of the polymer. According to one exemplary embodiment, the polymer consists essentially of a polymer of one or more $C_1$-$C_4$ alkyl (meth)acrylate monomers. According to another exemplary embodiment, the polymer consists essentially of a copolymer of $C_1$-$C_4$ (meth)acrylate and of (meth)acrylic acid or maleic anhydride.

By way of non-limiting example only, the polymer of the particles in the oil dispersion, which may optionally be crosslinked or alternatively may not be crosslinked, may be chosen from methyl acrylate homopolymers, ethyl acrylate homopolymers, methyl acrylate/ethyl acrylate copolymers, methyl acrylate/ethyl acrylate/acrylic acid copolymers, methyl acrylate/ethyl acrylate/maleic anhydride copolymers, methyl acrylate/acrylic acid copolymers, ethyl acrylate/acrylic acid copolymers, methyl acrylate/maleic anhydride copolymers, and ethyl acrylate/maleic anhydride copolymers.

The polymer of the particles in the dispersion may have a number-average molecular weight ranging from about 2000 to about 10,000,000, for example ranging from about 150,000 to about 500,000. The polymer particles may be present in the oil dispersion in a content ranging from about 20% to about 60%, for example about 21% to about 58.5%, about 30% to about 50%, about 35% to about 45%, or about 36% to about 42%, by weight, relative to the total weight of the oil dispersion.

The stabilizer in the oil dispersion may be an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than about 4, for example greater than about 4.5, or greater than about 5. For example, the weight ratio may range from about 4.5 to about 19, such as from about 5 to about 19, or from about 5 to about 12.

By way of example only, the stabilizer may be chosen from isobornyl acrylate homopolymers, statistical copolymers of isobornyl acrylate/methyl acrylate, statistical copolymers of isobornyl acrylate/methyl acrylate/ethyl acrylate, and statistical copolymers of isobornyl methacrylate/methyl acrylate.

In various embodiments, the stabilizer may have a number-average molecular weight ranging from about 10,000 to about 400,000, such as from about 20,000 to about 200,000.

In various embodiments, the combination of the stabilizer+polymer of the particles present in the oil dispersion comprises from about 10% to about 50%, such as about 15% to about 30%, by weight of polymerized isobornyl (meth) acrylate, and from about 50% to about 90%, such as about 70% to about 85%, by weight of polymerized $C_1$-$C_4$ alkyl (meth)acrylate, relative to the total weight of the combination of the stabilizer+polymer of the particles.

The oily medium of the oil dispersion comprises a hydrocarbon-based oil. The hydrocarbon-based oil is an oil that is liquid at room temperature (25° C.). The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

Exemplary and non-limiting embodiments of the hydrocarbon-based oil medium of the oil dispersion include hydrocarbon-based oils containing up to about 40, such as from 8 to 16 or from 8 to 14, carbon atoms. Optionally, the hydrocarbon-based oil is apolar. For example, the hydrocarbon based oil may be chosen from isododecane.

The oil dispersion may be prepared, for example, as described in WO2015/091513.

Alternatively, the adhesive polymer may be chosen from aliphatic or cycloaliphatic hydrocarbon polymers selected from aliphatic or cycloaliphatic hydrocarbon resins having a $T_g$ greater than about 25° C. By "aliphatic or cycloaliphatic hydrocarbon resins," it is meant polymers or copolymers of olefins or polymers or copolymers of partly or totally hydrogenated aromatic hydrocarbon monomers. For example, the adhesive polymer may be chosen from aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and hydrogenated styrene/methyl styrene/indene copolymers. In various embodiments, hydrogenated indene/methylstyrene/styrene copolymers marketed under the name of REGALITE® by Eastman Chemical, may be chosen. For example, REGALITE® R1090, REGALITE® R1100, REGALITE® S1100, REGALITE® R7100, REGALITE® R1010, REGALITE® R112, or REGALITE® S5100 may be chosen. As further examples, those sold under the name of ARKON® P-90, ARKON® P-100, and ARKON® P-115, by Arakawa, may be chosen.

In further embodiments, the adhesive polymer may have a $T_g$ of less than about 25° C. For example, the at least one adhesive polymer may be chosen from polyacids, such as hyperbranched polyacids. Polyacids useful according to various embodiments of the disclosure may be found in U.S. Pat. No. 7,582,719 and US2013/0236409, both of which are incorporated by reference herein.

The term "hyperbranched polyacid" refers to the fact that the functional groups of the hyperbranched functional polymer are substituted with carboxylic acid groups. Unsaturated functionalizing compounds useful include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

In various embodiments, the hyperbranched polyacid compound useful according to the disclosure may have at least two carboxyl groups. In various embodiments, the hyperbranched polyacid has a carboxyl number of at least 3, such as at least 10, at least 50, at least 100, or at least about 150. According to various embodiments, the hyperbranched polyacid has a carboxyl number ranging from about 50 to about 250, such as ranging from about 75 to about 225, about 100 to about 200, or about 125 to 175. In one embodiment, the hyperbranched polyacid has a carboxyl number ranging from 90 to 150.

In various embodiments, the at least one hyperbranched acid compound has a molecular weight (Mw) ranging from about 500 to about 25,000, such as ranging from about 800 to about 10,000, or from about 1000 to about 8000. In one embodiment, the hyperbranched polyacid has a Mw ranging from about 1000 to about 6000.

In various embodiments, the at least one hyperbranched polyacid compound has a viscosity at 210° F. ranging from 0.01 Pas to 10 Pas, such as from 0.02 to 7 Pas, or from 0.03 to 6 Pas, including all ranges and subranges there between. The viscosity is determined using Brookfield viscometer at 210° F. by ASTMD-3236MOD method. In various embodiments, the at least one hyperbranched acid compound has an acid number ranging from about 20 to about 400 mg/KOH, such as from about 30 to about 300 mg/KOH, or ranging from about 50 to about 100 mg/KOH.

In one exemplary embodiment, the at least one adhesive polymer is a polyacid chosen from $C_{30+}$ olefin/undecylenic acid copolymers, such as $C_{28}$-$C_{52}$ olefin/undecylenic acid copolymers, for example those available from New Phase Technologies under trade name Performa V6112™.

As yet further examples of adhesive polymers that may be chosen are acrylic type film formers. As used herein, "acrylic type film formers" include polymers that are film forming agents and which are based upon one or more (meth)acrylic acid (and corresponding (meth)acrylate) monomers or similar monomers.

Non-limiting examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms may be chosen. Examples of monomers of this kind include n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is possible to use monomers having functional groups selected from hydroxyl, carboxyl, sulphonic acid groups, phosphonic acid groups, acid anhydrides, epoxides, and amines. Examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, exemplary monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butylphenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, octafluoropentyl acrylate, octafluoropentyl methacrylate, 2,2,2-trifluoroethyl methacrylate, 1,1,1,3,3,3-hexafluoroisopropyl acrylate, 1,1,1,3,3,3-hexafluoroisopropyl methacrylate, 2,2,3,3,3-pentafluoropropyl methacrylate, 2,2,3,3,4,4,4-hexafluorobutyl methacrylate, 2,2,3,3,4,4,4-heptafluorobutyl acrylate, 2,2,3,3,4,4,4-heptafluorobutyl methacrylate, 2,2,3,3,4,4,5,5,6,6,7,7,8,8,8-pentadecafluorooctyl methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight, Mw, of 4000 to 13 000 g/mol), poly (methyl methacrylate)ethyl methacrylate (Mw of 2000 to 8000 g/mol).

As exemplary acrylic type film formers, mention may be made of copolymers of acrylic acid, isobutyl acrylate and isobornyl acetate, such as that sold under the names Pseudoblock (Chimex) and Synamer-3. In both of these commercial products, the copolymer is present with a solvent in a 1:1 ratio (50% solid). Another exemplary film former is Poly (isobornyl methacrylate-8 co-isobornyl acrylate-co-isobutyl acrylate-co-acrylic acid) at 50% of active material in 50% of octyldodecyl neopentanoate (Mexomere PAZ from Chimex)

Fillers

The compositions comprise at least one filler. The fillers may be mineral or organic in nature, and of any shape. In various embodiments, the fillers may have a particle size greater than about 100 nm, and/or a specific surface area greater than about 200 m$^2$/g.

By way of non-limiting example, fillers may be chosen from talc, mica, silica, silica surface-treated with a hydrophobic agent, fumed silica, kaolin, polyamide (Nylon®) powders (e.g. Orgasol® from Atochem), polyurethane powders, poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate.

In at least certain embodiments, the at least one filler may be chosen from hydrophobic silica aerogel particles. Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass ($S_M$) ranging from 500 to 1500 m$^2$/g, preferably from 600 to 1200 m$^2$/g and better still from 600 to 800 m$^2$/g, and a size expressed as the mean volume diameter (D[0.5]), ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

The silica aerogel particles used in the present invention may advantageously have a tamped density r) ranging from 0.04 g/cm$^3$ to 0.10 g/cm$^3$ and preferably from 0.05 g/cm$^3$ to 0.08 g/cm$^3$.

In the context of the present invention, this density, known as the tamped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in cm$^3$ and m in g).

According to one embodiment, the hydrophobic silica aerogel particles used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$ The specific surface area per unit of volume is given by the relationship:

$S_V = S_{M.r}$ where r is the tamped density expressed in g/cm$^3$ and $S_M$ is the specific surface area per unit of mass expressed in m$^2$/g, as defined above Preferably, the hydrophobic silica aerogel particles according to the invention have an oil-absorbing capacity, measured at the wet point, ranging from 5 to 18 mL/g, preferably from 6 to 15 mL/g and better still from 8 to 12 m L/g The oil-absorbing capacity measured at the wet point, noted Wp, corresponds to the amount of water that needs to be added to 100 g of particle in order to obtain a homogeneous paste It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in mL) of oil used is then noted The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups.

As hydrophobic silica aerogels that may be used in the invention, examples that may be mentioned include the aerogel sold under the name VM-2260 (INCI name: Silica silylate), by the company Dow Corning, the particles of which have a mean size of about 1000 μm and a specific surface area per unit of mass ranging from 600 to 800 m$^2$/g.

In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1100®, and Enova Aerogel MT 1200®, may be chosen.

Use will be made more particularly of the aerogel sold under the name VM-2270 (INCI name: Silica silylate), by the company Dow Corning, the particles of which have a mean size ranging from 5-15 μm and a specific surface area per unit of mass ranging from 600 to 800 m$^2$/g. It has an oil absorption capability of 1090 mL/100 g based on isononyl isononanoate.

Optionally, mixtures of fillers may be present in the compositions according to the disclosure. For example, a mixture of different aerogel particles, or of an aerogel and a different type of filler, may be used.

The at least one filler may be present in a total amount ranging from about 0.1% to about 20% by weight, for example from about 0.2% to about 15%, from about 0.5% to about 10%, or from about 1% to about 6%, by weight, relative to the total weight of the composition. In at least certain exemplary embodiments, the filler is present in an amount less than about 5%, such as less than about 4%, by weight, relative to the total weight of the composition. In one embodiment, the filler is present in an amount up to about 3% by weight, relative to the total weight of the composition Additional Components The compositions according to the disclosure may optionally further comprise additional components, such as solvents, silicone elastomers, humectants, and water Solvents The compositions may comprise at least one solvent. Optionally, the compositions may comprise at least one solvent chosen from solvents having a vapor pressure at room temperature (25° C.) of greater than about 100 Pa, such as greater than about 500 Pa, or greater than about 1000 Pa. In various embodiments, the composition is free or substantially free of solvents having a vapor pressure at room temperature (25° C.) of less than about 25 Pa. In further embodiments, the composition may comprise at least one solvent having a vapor pressure at room temperature (25° C.) of greater than about 100 Pa, such as greater than 500 Pa, or greater than 1000 Pa, and at least one solvent having a vapor pressure at room temperature (25° C.) of less than about 100 Pa, such as less than about 50 Pa, or less than about 25 Pa.

In various embodiments, the compositions comprise at least one volatile organic solvent. The volatile organic solvent may be chosen from, for example, volatile hydrocarbon-based oils and volatile silicone oils.

For example, volatile hydrocarbon oils include, but are not limited to, those having from 8 to 16 carbon atoms and their mixtures, such as branched $C_8$ to $C_{16}$ alkanes and $C_8$ to $C_{16}$ isoalkanes (also known as isoparaffins), isododecane, isodecane, isohexadecane. For example, the at least one solvent may be chosen from the oils sold under the trade names of Isopar® or Permethyl®, the $C_8$ to $C_{16}$ branched esters such as isohexyl or isodecyl neopentanoate and their mixtures. In at least certain embodiments, the volatile hydrocarbon oils have a flash point of at least 40° C. It is also possible to use mixtures of isoparaffins and other volatile hydrocarbon-based oils, such as petroleum distillates.

Further, volatile silicone oils may be chosen from linear or cyclic silicone oils, such as those having a viscosity at room temperature (25° C.) of less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclo-pentasiloxane, dodecamethylcyclohexasiloxane, heptamethyloctyltrisiloxane, hexamethyldisiloxane, decamethyltetrasiloxane, dodecamethylpentasiloxane, and their mixtures. In at least certain embodiments, the volatile silicone oils have a flash point of at least 40° C.

Additionally, the at least one volatile solvent may be chosen from polar volatile solvents, including but are not limited to, alcohols, volatile esters and volatile ethers.

The at least one solvent may be present in the composition in an amount up to about 95%, such as up to about 90%, up to about 85%, up to about 80%, up to about 75%, up to about 70%, up to about 65%, up to about 60%, up to about 55%, or up to about 50%, by weight of the composition. For example, the at least one solvent may be present in the composition in an amount ranging from about 40% to about 95%, such as about 50% to about 90%, or about 60% to about 85%, or about 65% to about 80%

Silicone Elastomer

The composition may further optionally comprise at least one silicone elastomer. Surprisingly, in certain embodiments, the at least one silicone elastomer may improve properties such as the thickness and water-resistance of the film, without significantly affecting the mechanical or optical properties of the film. In other embodiments, the addition of at least one silicone elastomer may decrease wettability by sebum, which will help prevent the film from losing tightening properties. It may, in at least certain embodiments, be advantageous to choose a silicone elastomer having greater than 1% active material (AM), such as greater than 2% AM.

The at least one silicone elastomer may, for example, be chosen from at least one silicone crosspolymer dispersed in at least one oil. The at least one silicone crosspolymer may, in certain embodiments, be chosen from dimethicone crosspolymers, such as dimethicone/vinyl dimethicone crosspolymers and dimethicone/phenyl vinyl dimethicone crosspolymers. In other embodiments, the silicone crosspolymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and C30-C45 alkyl cetearyl dimethicone cross-polymers. Non-limiting examples of polyether modified silicone cross-polymers include dimethicone/PEG-10/15 cross-polymers. Exemplary alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

In at least certain embodiments, the silicone polymers do not comprise polyethylene glycol or polypropylene groups, or hydrophilic moieties. Optionally, the silicone elastomer may be chosen from the silicone organic blends isododecane (and) dimethicone crosspolymer (18% AM) sold under the name EL-8040 ID or dimethicone/bis-isobutyl PPG-20 crosspolymer (17% AM in isododecane) sold under the name EL-8050 ID, by Dow Corning; or isododecane (and) vinyldimethyl/trimethylsiloxysilicate stearyl dimethicone crosspolymer (20% AM in isododecane), sold under the name GEL BELSIL RG90 by Wacker.

The silicone crosspolymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, for example, octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, for example, cetyl dimethicone and lauryl trimethicone; aryl derivatives of linear organopolysiloxanes, for example, phenyl trimethicone; and hydroxylated derivatives of linear organopolysiloxanes, for example, dimethiconol. In other embodiments, the oil may be chosen from organic oils, such as mineral oil; linear and branched alkanes, for example, isododecane; triethylhexanoin; and squalane.

The at least one silicone crosspolymer may, in some embodiments, comprise from about 5% to about 35% by weight, relative to the total weight of the silicone elastomer blend, for example, from about 10% to about 20% by weight, or from about 25% to about 35% by weight, or from about 20% to about 30% by weight. The at least one oil may comprise from about 65% to about 95% by weight, relative to the total weight of the silicone elastomer blend, such as from about 80% to about 90% by weight, or from about 65% to about 75% by weight, or from about 70% to about 80% by weight.

In various exemplary embodiments, the silicone elastomer blend comprises from about 20% to about 30% of dimethicone/vinyl dimethicone cross-polymer. In further exemplary embodiments, the silicone elastomer blend comprises from about 70% to about 80% by weight of dimethicone. In yet further exemplary embodiments, the silicone elastomer blend comprises from about 20% to about 30% of dimethicone/vinyl dimethicone cross-polymer and from about 70% to about 80% by weight dimethicone.

For example, silicone elastomers sold under the name KSG-16 dimethicone (and) dimethicone/vinyl dimethicone crosspolymer, KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% in active material) INCI name: Lauryl PEG-15 Dimethicone vinyl dimethicone crosspolymer), KSG-32 or KSG-42 or KSG-320 or KSG-30 (at 25% in active material) INCI name: Lauryl PEG-15 Dimethicone vinyl dimethicone crosspolymer), KSG-33: Lauryl PEG-15 (at 20% in active material) Dimethicone vinyl dimethicone crosspolymer), KSG-210 (at 25% in active material) INCI name: Dimethicone/PEG-10/15 crosspolymer), KSG-310: lauryl modified polydimethylsiloxane polyoxyethylenated in mineral oil, KSG-330 and KSG-340: PEG-15/lauryl dimethicone crosspolymer, and X-226146 (at 32% % in active material) INCI name: Dimethicone/PEG-10 Dimethicone vinyl dimethicone crosspolymer), all by Shin Etsu; DC9010 (at 9% in active material) and DC9011 (at 11% in active material) INCI name: PEG-12 dimethicone crosspolymer), DC9040 cyclopentasiloxane (and) dimethicone crosspolymer, and DC9041 dimethicone (and) dimethicone crosspolymer, all by Dow Corning; or the products sold under the VELVESIL product line by Momentive, such as VELVESIL 125 and VELVESIL DM, may be chosen.

Other examples of silicone elastomers include KSG-710 (at 25% in active material, INCI name: dimethicone/polyglycerin-3 crosspolymer); and KSG-820, KSG-830 and KSG-840, all of which are dimethicone/polvaleverin-3 crosspolymer (INCI), but in different diluents, 820 is in isododecane, 830 is in triethyl hexanoin, and 840 is in squalene, all by Shin Estu.

The at least one silicone elastomer may optionally be included in the composition in an amount up to about 10%, such as up to about 8%, up to about 5%, about 4.5%, up to about 4%, up to about 3.5%, up to about 3%, up to about 2.5%, up to about 2%, up to about 1.5%, up to about 1%, up to about 0.75%, up to about 0.5%, up to about 0.25%, up to about 0.2%, or up to about 0.1%, by weight, relative to the weight of the composition. In certain embodiments, the at least one silicone elastomer may be present in an amount ranging from about 1% to about 10%, such as about 2% to about 8%, about 3% to about 6%, or about 4% to about 5%, by weight, relative to the weight of the composition Humectants Optionally, compositions according to the disclosure may comprise at least one humectant or moisturizing agent. Surprisingly, in at least certain embodiments, the at least one humectant may improve the optical properties and feeling of the film formed on the skin by the composition, without negatively affecting the mechanical properties of the film.

By way of example only, humectants or moisturizing agents may be chosen from polyhydroxy compounds including but not limited to glycerin and glycols such as, for example, propylene glycol, butylene glycol, dipropylene glycol and diethylene glycol, glycol ethers such as monopropylene, dipropylene and tripropylene glycol alkyl($C_1$-$C_4$) ethers, monoethylene, diethylene and triethylene glycol.

The at least one humectant may be present in the composition in an amount up to about 20%, such as up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, up to about 1%, or up to about 0.5%, by weight of the composition Water Optionally, in at least certain embodiments, water may be added to the compositions according to the disclosure. Surprisingly, in certain non-limiting embodiments, water may improve the properties of the film formed on the skin by the composition, such as Young Modulus, transparency, cohesion, and thickness.

Water can be included in the composition in an amount up to about 15%, up to about 12%, up to about 10%, up to about 9%, up to about 8%, up to about 7%, up to about 6%, up to about 5%, up to about 4%, up to about 3%, up to about 2%, up to about 1%, or up to about 0.5%, by weight of the composition. In at least certain embodiments, the compositions are anhydrous or substantially anhydrous. In other embodiments, the compositions may be in the form of a water-in-oil (W/O) emulsion.

It may, in at least certain embodiments, be advantageous to include water and at least one humectant, for example water and glycerin, in the composition together Film When the compositions according to the disclosure are applied to the skin, the at least one thermoplastic elastomer, the at least one adhesive polymer, and the at least one filler together form a matrix that creates a film on the skin. The films formed by the compositions described herein form quickly, are long-lasting and durable, and have optical properties that are advantageous for a skin-tightening film, such as transparency, matte effect, and a soft focus effect which helps to blur skin imperfections so that they are less noticeable.

Additionally, as discussed above, the compositions according to the disclosure form a film that is stiffer than, and thus capable of tightening, human skin. Human skin has a Young Modulus in the range of 10 kPa to 100 kPa; thus, a film for tightening the skin should have a Young Modulus of greater than 100 kPa. The films that are formed by the compositions have Young Modulus' greater than 500 kPa (0.5 MPa) in some embodiments, greater than 1000 kPa (1 MPa) in some embodiments, greater than 5000 kPa (5 MPa) in some embodiments, and even greater than 10,000 kPa (10 MPa) in some embodiments. Additionally, the compositions according to the disclosure have sufficient consistency G* and phase angle below 45°, in order to form an effective and lasting film on the skin.

As such, the amounts and components of the composition should be chosen to provide a film on the skin that is capable of tightening the skin, while also blurring skin imperfections.

In various exemplary embodiments, for the best film properties, it may be advantageous for the total amount of thermoplastic elastomer plus adhesive polymer plus filler to be greater than about 10%, such as greater than about 15% or greater than about 20%, by weight, of the total weight of the composition.

In yet further exemplary embodiments, for the best film properties, it may be advantageous for amounts of the thermoplastic elastomer and adhesive polymer to be chosen so that the ratio of thermoplastic elastomer:adhesive polymer is in the range of about 1:10 to 10:1, in the range of about 1:5 to 5:1, or in the range of about 1:1 to 8:1.

The films may be formed quickly, for example within less than about 30 minutes, less than about 20 minutes, less than about 10 minutes, or less than about 5 minutes, after the composition is applied to the skin.

Films according to the disclosure may be long-lasting. For example, once the composition is applied to the skin and a film is formed, the film may remain substantially intact on the skin for a period of at least about 12 hours, such as at least about 24 hours, at least about 48 hours, or at least about 72 hours.

The films may also be durable. For example, the film may not rub off, may not come off with sweat, or when the film is contacted by water, makeup, lotions, or other products that the user may wish to put on the skin Sunscreen Compositions The sunscreen compositions may include:

(i) about 1 to about 40 wt. %, preferably about 5 to about 35 wt. %, more preferably about 10 to about 30 wt. %, based on the total weight of the sunscreen composition, of at least one (and preferably a plurality of) organic UV filters selected from a para-aminobenzoate derivative, a salicylate derivative, a cinnamate derivative, a benzophenone or an aminobenzophenone, an anthranillate derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof, wherein the sunscreen composition preferably includes at least one UVA filter and at least one UVB filter, thereby providing full spectrum protection from UV radiation; and (ii) about 30 to about 90 wt. %, preferably about 40 to about 85 wt. %, based on the total weight of the sunscreen composition, of more preferably about 50 to about 80 wt. % of a cosmetically acceptable carrier.

UV Filters

UV filters are well known in the art for their use in stopping UV radiation. For example, the UV filter may be one or more organic UV filters and/or one or more inorganic UV filters. Non-limiting examples of UV filters include:
  i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.
  ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
  iii. Inorganic UV filters such as titanium oxide and zinc oxide, iron oxide, zirconium oxide and cerium oxide; and
  iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

The total amount of UVA filters (both UVA1 and UVA2) in the sunscreen compositions, if present, may vary but is typically greater than zero to about 20 wt. %, based on the total weight of the sunscreen composition. In some cases, the total amount of UVA filters in the cosmetic compositions is from about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 1 to about 20 wt. %, about 1 to about 15 wt. %, about 1 to about 10 wt. %, about 1 to about 8 wt. %, about 1 to about 6 wt. %, or about 1 to about 5 wt. %, based on the total weight of the cosmetic composition.

The sunscreen compositions include at least one organic UVB filter. In some instances it is preferable to include more than one organic UVB filter, for example, at least 2, 3, 4, or 5 UVB filters. Non-limiting examples of UVB filters include a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and mixtures thereof.

In some instances, at least one UVB filter may be selected from the group consisting of methylene bis-benzotriazolyl tetramethylphenol (Tinosorb M), diethylamino hydroxybenzoyl hexyl benzoate, ethylhexyl salicylate, ethylhexyl methoxycinnamate, isoamyl methoxycinnamate, polysilicone-15, menthyl anthranilate, ethylhexyl dimethyl PABA, aminobenzoic acid (PABA), cinoxate, dioxybenzone, ecamsule (Mexoryl SX), ensulizole (phenylbenzimiazole sulfonic acid), homosalate, meradimate (menthyl anhranilate), octocrylene, octinoxate (octyl methoxycinnamate), octisalate (octyl salicylate), oxybenzone, padimate O, sulisobenzone, trolamine salicylate, and a mixture thereof.

The sunscreen compositions of the present disclosure may optionally include one or more inorganic UV filters that provide protection from UVA and/or UVB radiation. In some instances, however, the sunscreen compositions of the present disclosure are free or essentially free of inorganic UVA and/or inorganic UVB filters.

The total amount of UVB filters in the sunscreen compositions of the present disclosure can vary and will depend on the desired SPF for the sunscreen composition. Higher amounts of UVB filters typically provide higher SPFs. In some instances, the total amount of UVB filters in the sunscreen compositions may be about 0.1 to about 40 wt. %, based on the total weight of the cosmetic composition. The total amount of UVB filters may be about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 1 to about 40 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, about 5 to about 40 wt. %, about 5 to about 35 wt. %, about 5 to about 30 wt. %, about 5 to about 25 wt. %, about 5 to about 20 wt. %, about 5 to about 15 wt. %, or about 5 to about 10 wt. %, based on the total weight of the sunscreen composition.

Cosmetically Acceptable Carrier

The sunscreen compositions include a cosmetically acceptable carrier. The phrase "cosmetically acceptable" means that the material is compatible with skin. For example, "cosmetically acceptable carrier" means a carrier that is compatible with skin and acceptable for application to the skin of the body, especially the skin of the face.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof Methods Methods of improving the appearance of the skin and protecting the skin from the sun damages are also disclosed, said methods comprising applying a skin tightening composition according to the disclosure onto the skin in order to form a film on the skin, then applying a sunscreen composition according to the disclosure on top of the skin tightening composition.

Methods of improving the appearance of the skin and protecting the skin from the sun damages are also disclosed, said methods comprising applying a sunscreen composition according to the disclosure onto the skin, then applying a skin tightening composition according to the disclosure on top of the sunscreen composition in order to form a film.

Methods comprise tightening the skin, e.g. to cover and flatten imperfections of the skin, scars, superficial facial scar tissue, unevenness of the skin, acne scars as well as protecting the skin from the sun damages by boosting the SPF when the two compositions are layered instead of being mixed in one formula.

It is to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

It is understood that when an amount of a component is given, it is intended to signify the amount of the active material.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

The foregoing description illustrates and describes the disclosure. Additionally, the disclosure shows and describes only the preferred embodiments and is capable of changes or modifications within the scope of the inventive concepts expressed herein, commensurate with the above teachings and/or the skill or knowledge of the relevant art. The embodiments described herein are intended to explain best modes and to enable others skilled in the art to utilize the disclosure in such, or other, embodiments and variations. Accordingly, the description is not intended to limit the invention. Also, it is intended that the appended claims are construed to include alternative embodiments.

As used herein, the terms "comprising," "having," and "including" are used in their open, non-limiting sense.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component).

The term "treat" (and its grammatical variations) as used herein refers to the application of the compositions of the present disclosure onto the surface of keratinous substrates such as skin, in particular, the skin of the head, face, and neck.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls

EXAMPLES

The following Examples are provided for illustrative purposes only, and are not intended to be limiting.

In each of the following examples, the amounts of components given are in terms of active material (AM)

Dynamic Mechanical Analysis (DMA)

The determination of Young Modulus of the films for all Examples was as follows. The film was made by using a draw down bar at 8 mil to cast the solution on a Teflon plate and dried the film at 40° C. in an oven overnight. The DMA Q800FR from TA instruments was used to measure the stress-strain response of the dried film. The deformation was applied from 0% strain to 200% strain at a rate of 100% strain/min at 32° C. Then the Young Modulus of the film was determined from the slope of the stress-strain curve in the linear viscoelastic regime.

Scanning Electron Microscope (SEM) Measurement

The film sample for SEM was made by using the same method as for DMA measurement. Subsequently, the film was cut into a 5×5 mm piece and loaded onto a stage with a double sided carbon tape. The sample was scanned with a Hitachi TM-1000 Tabletop SEM.

Rheology Measurement

The rheology of sample solutions was measured by using Rheometer AR-G2 from TA instruments. The dynamic oscillation mode was used with the parallel plate of 20 mm diameter at a gap of 200 μm.

The strain sweep from 0.001% to 1000% at an oscillation frequency of 1 rad/s was applied to the sample at 32° C. The value of elastic modulus G' and viscous modulus G" at 10% strain were recorded for each measured sample. The complex modulus G* (consistency) and phase angle δ collected at 10% strain (in linear viscoelastic regime) were calculated from the elastic modulus G' and viscous modulus G" by the following equations:

$$G^* = \sqrt{G'^2 + G''^2}$$

$$\delta = \arctan\left(\frac{G''}{G'}\right)$$

Haze and Transparency-BYK Haze-Guard

The film was made by using a draw down bar at 8 mil to cast the solution on a transparent plastic film and dried on bench for 3 hours. The BYK Haze-Guard instrument was used to measure the transparency and the haze of the film.

Gloss—BYK Glossmeter

The film was made by using a draw down bar at 8 mil to cast the solution on a transparent plastic film and dried on bench for 3 hours. The BYK Glossmeter was used to measure the gloss and matteness of the film Film Permeability The film was made by using a draw down bar at 8 mil to cast the solution on a Teflon plate and dried the film at 40° C. in an oven overnight. The film was peeled off and cut to 55 cm pieces. Each piece was used to cover the top of a scintillation vial filled with 2 mL water, and a piece of Parafilm was used to wrap the piece of film on the side. The weight of each vial was measured immediately as well as different time points. The water weight loss of different films was plotted to the different time points and the evaporation was calculated by fitting the evaporation curve with a linear function. The water vapor permeability of the film (P) is calculated with the followed equation, where (J) is the water vapor permeation flux; (l) is the thickness of the film and the (Δp) is the water vapor pressure difference between the space sealed by the film in the vial and the outside of the film, which is the ambient:

$$P = J(\Delta p/l)$$

Contact Angle Measurement

The film was made by using a draw down bar at 8 mil to cast the solution on a glass slide and dried on bench overnight. The contact angle of the film on the glass slide was measured by the Biolin Scientific Attension Tensiometer.

Speed of Drying

The film was made by using a draw down bar at 8 mil to cast the solution on a transparent plastic film and weighed regularly during a period of one hour.

Internal Constraint

A measured volume of formula is deposited and spread onto the nitrile band using a spatula or glass rod and let dry for a period of one hour. As the film shrinks upon drying, the surface of the nitrile band is measured by image analysis.

Transparency, Homogenizing Power and Whitening Power—Colorimeter MINOLTA

The film was made by casting the solution on a transparent plastic film using a draw down bar (2 mil) and left to dry on the bench for 1 hour. The Minolta colorimeter was used to measure the L, a*, b* and Y of the film, and of a skin tone sheet reference and black and white reference, in order to calculate the transparency, homogenizing power, and whitening power of the films.

Example 1: Association of Thermoplastic Elastomer, Adhesive Polymer, and Filler

A thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of oil dispersion (49% in isododecane), silica silylate, and UV protection agents were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

The following Table 1 shows a skin tightening formula prepared according to the procedure described above.

TABLE 1

| | Ex. 2a | Ex. 2b | Ex. 2c | Ex. 3d | Ex. 3e | Ex. 3f |
|---|---|---|---|---|---|---|
| Ratio-Kraton (AM):OD (AM) | 5 | 1 | 0.25 | 2 | 4 | 8 |
| HYDROGENATED STYRENE/ BUTADIENE COPOLYMER | 20.1% | 12.1% | 4.8% | 11.0% | 11.0% | 11.0% |
| OIL DISPERSION | 4.1% | 12.1% | 19.4% | 5.5% | 2.8% | 1.4% |
| SILICA SILYLATE | 3.0% | 3.0% | 3.0% | 3.0% | 3.0% | 3.0% |
| ISODODECANE | 38.3% | 38.3% | 38.3% | 47.5% | 50.3% | 51.6% |

TABLE 1-continued

| | Ex. 2a | Ex. 2b | Ex. 2c | Ex. 3d | Ex. 3e | Ex. 3f |
|---|---|---|---|---|---|---|
| C8-9 ISOPARAFFIN | 34.5% | 34.5% | 34.5% | 33.0% | 33.0% | 33.0% |
| Total | 100.0% | 100.0% | 100.0% | 100.0% | 100.0% | 100.0% |
| G*(10% strain) Pa | 3389.3 | 1772 | 386.9 | | | |
| δ (10% strain) ° | 34.8 | 35 | 31.5 | | | |
| Young Modulus (Mpa) at 32° C. | 13.7 | 29.8 | 78.2 | 38.2 | 29.9 | 20.9 |
| CONCLUSION ON FILM PROEPERTIES | Acceptable | Good | Good | Good | Good | Good |

Example 2: Preparation of a Sunscreen Composition

The sunscreen compositions may be prepared by preparing a water phase combining oil-miscible, oil-soluble, and oil-dispersible ingredients in a beaker or other suitable vessel and heating to about 50° C. to about 70° C. while mixing. In a similar way an oil phase may be prepared by combining, water-miscible, water-soluble, and water-dispersible ingredients in a beaker or other suitable vessel and heating to about 50° C. to about 70° C. while mixing. Both oil phase and water phase are combined by transferring one phase into the other while mixing via homogenization and maintaining a temperature of about 50° C. to about 70° C. The oil phase may be added to the water phase or vice versa. The combined oil phase and water phase are homogenized for about 20 minutes and the mixture is cooled to room temperature. Preferably, additional ingredients such as polymers, fillers, emollients or other aesthetic modifiers, actives and preservatives may be added once the temperature of the mixture is below about 40° C. while mixing.

The following Table 2 shows a sunscreen formula prepared according to the procedure described above.

TABLE 2

| Sunscreen (Oil-in-Water Emulsion) | | Ex. 1 |
|---|---|---|
| | INCI US | |
| UVA Filter | AVOBENZONE | 3 |
| UVB Filters | HOMOSALATE | 5 |
| | ETHYLHEXYL SALICYLATE | 4 |
| | OCTOCRYLENE | 5 |
| Nonionic Emulsifier | GLYCERYL STEARATE (and) PEG-100 STEARATE | 3 |
| Film Forming Polymer | ACRYLATES COPOLYMER | 0.4 |
| pH Adjustment | TRIETHANOLAMINE | 0.2 |
| Miscellaneous | Preservative(s), chelating agent(s), Vitamin(s), etc. | ≤3 |
| Carrier | WATER | 75.8 |

Example 3: Evaluation of SPF and Film Formation

TABLE 3

The integrity of the film and the SPF values were measured in different Experiments and are presented in the Table below.

| Experiment | Examples | Description | Deposit contains UV Filters | Relative Film Integrity[1] | SPF in vitro[2] |
|---|---|---|---|---|---|
| 1 | Ex. 1 | Sunscreen composition (20 mg) containing organic UV filters Alone | YES | NO | 11.14 12.20 |
| 2 | Ex. 2 | Skin tightening composition (200 mg) | NO | YES | 0.67 0.62 |
| 3 | Ex. 3 | Ex. 1 (20 mg) + Ex. 2 (200 mg) on top Ex. 1 | YES | YES | Greater than 250* |
| 4 | Ex. 4 | Ex. 2 (200 mg) + Ex. 1 (20 mg) on top of Ex. 2 | YES | YES | Greater than 250* |
| 5 | Ex. 5 | 1:10 by wt of Ex. 1 + Ex. 2 mixed before application | YES | NO | Greater than 250* |

[1]Film integrity observed by running finger over PMMA plate after application. The presence of film integrity indicates that the surface is smooth, and not tacky, and is implicative of a cohesive film that would be required for a tightening effect on skin.
[2]Each experiment was run in duplicate. Both values are shown.
*SPF values measured in vitro include absorption values at some wavelengths which were above the detection limit of the instrument.

The SPF was measured using a Labsphere 2000S UV analyzer in a manner adapted from that of Fageon et al (International Journal Of Cosmetic Science, Volume 31, Issue 6, December 9, Pages 405-418). Each sample was added to the rough surface of a 5 cm×5 cm PMMA plate. For the sunscreen composition, an amount of 20 mg was added to the 25 cm2 PMMA plate. For the Skin tightening composition, an amount of 200 mg was added, as this was necessary in order to create an intact film after application of the sample to the PMMA plate. In fact, any amount of skin tightening composition applied under 200 mg was unable to be spread evenly on the surface of the PMMA plate. For Ex. 5, the sunscreen composition and skin tightening composition were first combined and mixed with a spatula in a separate container in a 1:10 weight ratio of sunscreen composition to skin tightening composition, and then 220 mg of said mixture was added to the PMMA plate. The sunscreen composition in Ex. 1 was evenly spread onto the PMMA plate using a circular motion following by a horizontal spreading motion. The Skin tightening compositions described in Ex. 2, 3, and 4, and the mixture described in Ex. 5 were evenly spread onto the PMMA plate by first holding a flat spatula or separate clean PMMA plate at a 45° angle relative to the plate containing the sample and then applying a smooth horizontal motion parallel to the surface of the PMMA plate in order to spread the sample evenly across the plate. All plates were left to dry for 15 to 20 minutes before measurement or before applying any additional samples to be layered onto the plate. After drying, the treated plates were analyzed using a Labsphere 2000S analyzer at 5 different locations on the plate.

Relative Film Integrity was measured for samples applied to the PMMA plate by gently rubbing a finger over the PMMA plate after the samples were left to dry for 15 to 20 minutes. A value of "YES" for Relative Film Integrity in Table 3 was recorded if after gently rubbing the surface of the sample-covered PMMA plate with 5 to 10 horizontal motions, the resulting film was left undisturbed, intact, and was smooth and not tacky to the touch. Samples which demonstrated this type of integrity on PMMA also demonstrated skin tightening when applied to skin surfaces such as the volor forearm or back of the hand. A value of "NO" for Relative Film Integrity in Table 3 was recorded if gently rubbing the surface of the sample resulted in destruction of the film on the PMMA plate, which was observed in all cases where a value of "NO" was recorded after about 2 to 5 horizontal motions on the PMMA plate.

In vitro SPF was calculated according to the method indicated in Fageon et al (International Journal Of Cosmetic Science, Volume 31, Issue 6, December 9, Pages 405-418) following measurement with a Labsphere 2000S UV analyzer. All in vitro SPF values recorded in Table 1 represent an average of each experiment run in duplicate.

Ex. 1 did not demonstrate Relative Film Integrity, which is indicative that the formula would not create a cohesive film and result in tightening properties when on skin as expected for sunscreen composition when applied alone. The in vitro SPF value measured for Ex. 1 is within the expected range, given the amount and kind of UV filters contained within the sunscreen composition.

In Ex. 2, the skin tightening composition exhibited a good Relative Film Integrity, which is indicative of the formula forming a cohesive film and demonstrating skin tightening properties. As expected, the skin tightening composition does not exhibit any sun protection properties on its own as indicated by the low measured in vitro SPF value, since this formula does not contain UV filters.

In Ex. 3, the sunscreen composition was applied first to the PMMA plate in the same manner described above and used in Ex. 1. After allowing to dry for 15 to 20 minutes, the Skin tightening composition was applied to the same plate on top of the sunscreen composition in the manner described above and was left to dry for 15 to 20 minutes. The resulting layered film in Ex. 3 exhibited good relative film integrity that was indistinguishable from that measured in Ex. 2. Surprisingly the SPF values measured in Ex. 3 were high enough to be above that which was measurable using the Labsphere 2000S UV analyzer. Ex. 3 demonstrated that layering of the skin tightening composition over the sunscreen composition boosted the SPF values without compromising the formation of the film and compromising the tightening effect and film integrity, making it very interesting in term of use for both, sunscreen composition and desired skin transformations which may include anti-wrinkle, skin tightening, and/or skin plumping or volumizing.

In Ex. 4, the skin tightening composition was applied first to the PMMA plate in the same manner described above and used in Ex. 2. After allowing to dry for 15 to 20 minutes, the sunscreen composition was applied to the same plate on top of the skin tightening composition in the manner described above and was left to dry for 15 to 20 minutes. The resulting layered film in Ex. 4 exhibited good relative film integrity that was indistinguishable from that measured in Ex. 2. Surprisingly the SPF values measured in Ex. 4 were high enough to be above that which was measurable using the Labsphere 2000S UV analyzer. Ex. 4 demonstrated that layering of the sunscreen composition over the skin tightening composition also boosted the SPF values, without compromising the formation of film and consequently the tightening effect, making it very interesting in term of use for both, sunscreen composition and desired skin transformations which may include anti-wrinkle, skin tightening, and/or skin plumping or volumizing.

In Ex. 5, the sunscreen composition and skin tightening composition were mixed together in a 1:10 weight ratio of sunscreen composition to skin tightening composition before application to the PMMA plate. The ratio and amount of sunscreen composition and skin tightening composition used in Ex. 5 were chosen to be identical to the total amount and ratio of said sunscreen composition and said skin tightening compositions used in Ex. 3 and Ex. 4. Therefore, Ex. 5 represents the scenarios of Ex. 3 and Ex. 4 wherein said sunscreen composition and said skin tightening composition are not applied as separate layers to the PMMA plate, but applied as a mixture. Surprisingly the SPF values measured in Ex. 5 were high enough to be above that which was measurable using the Labsphere 2000S UV analyzer. However, even though the mixture of sunscreen composition and skin tightening composition used in Ex. 5 contained the skin tightening composition, the relative film integrity was low and indicated that this mixture failed to create a cohesive film capable of a skin tightening effect.

In conclusion, the experiments described in Table 3 and above demonstrate that layering a sunscreen composition and a skin tightening composition comprising at least one thermoplastic elastomer and at least one adhesive polymer, boosted the SPF values without compromising the formation of the film. This was not the case when the two compositions were mixed, i.e. in Experiment #5. Ex. 5 demonstrated that when the sunscreen composition and skin tightening composition are mixed, only the boost of SPF values is observed, whereas the skin tightening effect is removed.

What is claimed is:

1. A method for treating the skin by applying onto the skin:
    (a) a skin tightening composition comprising:
        i. at least one thermoplastic elastomer chosen from amorphous hydrocarbon block copolymers of styrene and monomers of hydrocarbon containing 2 to 5 carbon atoms and comprising one or two ethylenic unsaturations, and having a first $T_g$ below about 0° C., and a second $T_g$ greater than about 25° C.;
        ii. at least one adhesive film-forming polymer chosen from polymer particles of $C_1$-$C_4$ alkyl(methacrylate) polymer, stabilized in a non-aqueous dispersion; and
        iii. at least one filler, and
    (b) an oil-in-water sunscreen composition comprising:
        iv. one or more organic UV filters present from about 15 to about 40 wt. % based on the total weight of the sunscreen composition; and
        v. a cosmetically acceptable carrier,
    wherein the Young Modulus of the film formed on the skin is greater than about 500 kPa, and
    wherein the skin tightening composition and the sunscreen composition are layered.

2. The method of claim 1 comprising application of the skin tightening composition onto the skin, followed by application of the oil-in-water sunscreen composition onto the skin tightening composition.

3. The method of claim 1 comprising application of the oil-in-water sunscreen composition onto the skin, followed by application of the skin tightening composition onto the sunscreen composition.

4. The method of claim 1, wherein applying the skin tightening composition over the oil-in-water sunscreen composition increases the SPF in vitro by about 25 times relative to the application of the sunscreen composition alone.

5. The method of claim 1, wherein applying the oil-in-water sunscreen composition over the skin tightening composition increases the SPF in vitro by about 25 times relative to application of the sunscreen composition alone.

6. The method of claim 1, wherein applying the skin tightening composition over the oil-in-water sunscreen composition increases the SPF in vitro more than the SPF in vitro obtained by applying a mixture of the skin tightening composition and the oil-in-water sunscreen composition in the same ratio as the layered application of the skin tightening composition and the sunscreen composition.

7. The method of claim 1, wherein applying the oil-in-water sunscreen composition over the skin tightening composition increases the SPF in vitro more than the SPF in vitro obtained by applying a mixture of the skin tightening composition and the oil-in-water sunscreen composition in the same ratio as the layered application of the skin tightening composition and the sunscreen composition.

8. The method of claim 1, wherein the at least one thermoplastic elastomer is present in the composition in an amount ranging from about 5% to about 25% by weight, relative to the total weight of the composition.

9. The method of claim 1, wherein the one or more UV filters are selected from the group consisting of ethylhexyl salicylate, butyl methoxydibenzoylmethane, ethylhexyl methoxycinnamate, octocrylene, phenylbenzimidazole sulfonic acid, terephthalylidene dicamphor sulfonic acid, benzophenone-3, benzophenone-4, benzophenone-5, 4-methylbenzylidene camphor, benzimidazilate, anisotriazine, ethylhexyl triazone, diethylhexyl butamido triazone, methylene bis-benzotriazolyl tetramethylbutylphenol, drometrizole trisiloxane, and mixtures thereof.

10. The method of claim 1, wherein the oil-in-water sunscreen composition comprises at least two organic-UV filters.

11. The method of claim 10, wherein the oil-in-water sunscreen composition comprises at least one UVA filter and at least one UVB filter.

12. The method of claim 1, wherein the oil-in-water sunscreen composition is applied topically under the skin tightening composition.

13. The method of claim 1, wherein the oil-in-water sunscreen composition is applied topically over the skin tightening composition.

14. The method of claim 1, wherein the cosmetically acceptable carrier in the oil-in-water sunscreen composition comprises water.

\* \* \* \* \*